US010448732B2

(12) United States Patent
Asmuth et al.

(10) Patent No.: US 10,448,732 B2
(45) Date of Patent: Oct. 22, 2019

(54) DESK AND PROPRIOCEPTIVE FOOT STIMULATOR ASSEMBLY

(71) Applicant: School Specialty, Inc., Greenville, WI (US)

(72) Inventors: Tom Asmuth, Greenville, WI (US); Greg Saul, Charlotte, NC (US)

(73) Assignee: School Specialty, Inc., Greenville, WI (US)

( * ) Notice: Subject to any disclaimer, the term of this patent is extended or adjusted under 35 U.S.C. 154(b) by 0 days.

(21) Appl. No.: 15/889,801

(22) Filed: Feb. 6, 2018

(65) Prior Publication Data

US 2019/0239637 A1    Aug. 8, 2019

(51) Int. Cl.
| | | |
|---|---|---|
| *A47B 13/02* | (2006.01) | |
| *A61M 21/02* | (2006.01) | |
| A47B 9/20 | (2006.01) | |
| A61M 21/00 | (2006.01) | |
| A47B 21/02 | (2006.01) | |

(52) U.S. Cl.
CPC ............ *A47B 13/02* (2013.01); *A61M 21/02* (2013.01); *A47B 9/20* (2013.01); *A47B 21/02* (2013.01); *A47B 2200/0019* (2013.01); *A47B 2200/0088* (2013.01); *A47B 2200/0097* (2013.01); *A61M 2021/0022* (2013.01)

(58) Field of Classification Search
CPC ......... A47B 13/02; A47C 9/005; A47C 7/503; A47C 7/506; A47C 7/5062; A47C 7/5066
USPC .................... 108/50.01, 50.02, 20.14, 50.14; 297/423.12, 423.2, 423.22, 423.24, 297/423.35, 423.36, 408, 409, 410
See application file for complete search history.

(56) References Cited

U.S. PATENT DOCUMENTS

| | | | | |
|---|---|---|---|---|
| 1,652,774 A | * | 12/1927 | Fraser ................... | A47B 19/06 108/1 |
| 1,975,004 A | | 9/1934 | Jenkins | |
| 2,306,864 A | * | 12/1942 | Caesar ................... | A47C 7/40 297/423.15 |
| 3,375,039 A | * | 3/1968 | Gielow .................. | A47C 7/506 297/423.15 |
| 3,537,749 A | * | 11/1970 | Putsch ................... | B60N 2/853 297/408 |
| 3,632,169 A | * | 1/1972 | Barecki ................. | A47C 7/506 297/423.15 |

(Continued)

*Primary Examiner* — Jose V Chen
(74) *Attorney, Agent, or Firm* — Nicholas A. Kees; Godfrey & Kahn, S.C.

(57) ABSTRACT

A proprioceptive foot stimulator assembly having a cross bar that connects to the leg structure of a desk. The assembly includes a bottom channel that pivotably attaches to the cross bar, and a foot stimulating member that attaches to the bottom channel, so that it can pivot in relation to the crossbar. Mounting flanges are located at the longitudinal ends of the cross bar. A pivot assembly, generating the pivotable attachment between the bottom channel and the cross bar, includes two threaded fasteners and a bushing, secured by lock nuts; the bushing connecting the first threaded fastener to the second threaded fastener, such that the second threaded fastener can pivot in relation to the first threaded fastener. In another embodiment, the proprioceptive foot stimulator assembly has at least one slider track capable of being attached to a desk and a foot stimulating member that slidably connects to the slider track.

23 Claims, 4 Drawing Sheets

(56) References Cited

U.S. PATENT DOCUMENTS

| | | | |
|---|---|---|---|
| 3,961,822 A | 6/1976 | Daniel | |
| 4,190,290 A * | 2/1980 | Strien | B60N 2/853 |
| | | | 297/408 |
| 4,920,458 A * | 4/1990 | Jones | A47B 83/001 |
| | | | 248/917 |
| 4,971,393 A * | 11/1990 | Maisenhalder | A47C 7/383 |
| | | | 297/397 |
| 5,174,223 A * | 12/1992 | Nagy | A47B 21/00 |
| | | | 108/50.01 |
| 5,826,941 A | 10/1998 | Olsen | |
| 5,863,282 A * | 1/1999 | Moossun | A47B 17/00 |
| | | | 297/423.1 |
| 5,937,766 A * | 8/1999 | Denny | B25H 5/00 |
| | | | 108/143 |
| 6,418,862 B1 * | 7/2002 | Heil | B65D 19/0028 |
| | | | 108/57.12 |
| 6,732,660 B2 * | 5/2004 | Dame | A47B 13/003 |
| | | | 108/50.01 |
| 6,810,820 B1 * | 11/2004 | Okerlund | A47B 9/06 |
| | | | 108/137 |
| 7,509,696 B2 * | 3/2009 | Soto | A47C 7/70 |
| | | | 108/49 |
| 7,621,599 B2 * | 11/2009 | Whalen | A47C 7/50 |
| | | | 297/423.21 |
| 7,908,978 B1 * | 3/2011 | Pelton, Jr. | A47B 21/06 |
| | | | 108/50.01 |
| 8,061,278 B2 | 11/2011 | Skiba | |
| 8,291,833 B2 | 10/2012 | Skiba | |
| D671,771 S | 12/2012 | Heyvaerts | |
| 9,291,234 B1 * | 3/2016 | Green | B65D 19/40 |
| 2004/0065235 A1 * | 4/2004 | de Oliveira | A47B 21/00 |
| | | | 108/50.01 |
| 2005/0052067 A1 * | 3/2005 | Grimm | A47C 1/03211 |
| | | | 297/423.2 |
| 2006/0065163 A1 * | 3/2006 | Chi | A47B 21/03 |
| | | | 108/7 |
| 2008/0203801 A1 * | 8/2008 | Jammalamadaka | B60N 2/856 |
| | | | 297/408 |
| 2011/0227387 A1 * | 9/2011 | Kolich | B60N 2/58 |
| | | | 297/408 |
| 2014/0020606 A1 * | 1/2014 | Benden | A47B 13/00 |
| | | | 108/50.14 |
| 2014/0090581 A1 * | 4/2014 | Schultz | F16F 15/067 |
| | | | 108/57.12 |

\* cited by examiner

DESK AND PROPRIOCEPTIVE FOOT STIMULATOR ASSEMBLY

FIELD OF THE INVENTION

The present invention relates generally to desks and foot device assemblies, and in particular, to a proprioceptive foot stimulator assembly capable of stimulating a foot while a user sits at a desk or other work space without disrupting the working or learning environment surrounding the user.

BACKGROUND

A typical desk, whether configured for a sitting or a standing user, is configured with an empty cavity formed between a work surface of the desk and a floor on which the desk rests, such that the user may rest his or her feet on the floor while working at the desk. To improve the posture of the individual sitting or standing at a given desk, some desks have been configured to include a foot rest where a user may rest his or her foot in an elevated position. U.S. Pat. Nos. 3,961,822, 5,826,941, and D671771 disclose such foot rest configurations. While such foot rests may be adjustable, for instance allowing the user to adjust the height at which the user's foot rests, they are not configured to move in a manner that stimulates the user's foot while in use. Rather, the above foot rests merely provide a place for the foot to rest.

However, recent studies have shown that some desk users, particularly those struggling with poor proprioception, are able to improve their mental focus in learning and working environments through stimulation of their external limbs, such as their feet. Proprioception is often described as a sixth sense—the subconscious awareness of where the limbs of a body are positioned, even when those limbs are not activated or within view. A person with poor proprioception lacks this subconscious awareness. Hence, a brain lacking fully developed proprioception becomes easily distracted when trying and failing to locate input from inactive limbs of the body, such as from feet resting under a desk.

Presently, individuals with poor proprioception attempt to improve their mental focus through such actions as tapping their feet under their desks or rocking their front chair legs back while rocking their feet on the floor, using a physical stimulus to send their brains the same input that the sensory systems of an individuals with more developed proprioception would naturally send, even in the absence of external stimulation. However, such behaviors can cause disruptions, and as such, are often frowned upon in group learning or working environments. Therefore, a foot device assembly is needed to provide a quiet, non-distracting means of stimulating an individual desk user's foot under his or her desk.

One foot device assembly aimed at stimulating a user's foot under a desk is disclosed in U.S. Pat. Nos. 8,061,278 and 8,291,833. This device has a foot engageable support, including a rotatable pedal, connected to a pair of swinging elongated arms. The elongated arms swing below the desk, causing the foot engageable member to oscillate in a pendulum-like motion beneath the work surface of the desk. However, while possessing some foot stimulating potential, when installed on desks for younger students, such as $3^{rd}$, $4^{th}$, $5^{th}$, and $6^{th}$ graders, this foot device assembly still has a high potential for causing distractions in the learning environment. Some children of this age could kick and flip this foot device around to cause disruptions or to compete with friends over who can flip the foot device the highest. Additionally, the combination of the fully rotatable nature of the pedal with the oscillating nature of the foot device leads to a potential for the user's heel to hit the ground as the user swings his or her foot on the device, causing a distracting sound. As such, there is a need for a foot device assembly that can provide the necessary stimulus to allow a person with lesser developed proprioception to focus, while limiting further distraction or disruption in the surrounding learning or working environment.

This invention relates to improvements to some of the apparatus described above, and to solutions to some of the problems raised or not solved thereby.

SUMMARY OF THE INVENTION

The present invention relates to a desk having a proprioceptive foot stimulator assembly. According to the invention, the desk has a work surface, a leg structure that connects to and supports the work surface, and a proprioceptive foot stimulator assembly that connects to the leg structure. The proprioceptive foot stimulator assembly has a cross bar that connects to the leg structure, a bottom channel that pivotably attaches to the cross bar, and a foot stimulating member that attaches to the bottom channel, such that the foot stimulating member can pivot in relation to the crossbar. Mounting flanges capable of being affixed to a desk are located at the longitudinal ends of the cross bar. A pivot assembly generates the pivotable attachment between the bottom channel and the cross bar. Each pivot assembly includes a first threaded fastener, a second threaded fastener, and a bushing. A first lock nut secures the first threaded fastener to the cross bar; a second lock nut secures the second threaded fastener to the bottom channel; and the bushing connects the first threaded fastener to the second threaded fastener, such that the second threaded fastener can pivot in relation to the first threaded fastener.

In another aspect of this invention, the proprioceptive foot stimulator assembly has at least one slider track capable of being attached to a desk and a foot stimulating member that slidably connects to the slider track.

Other objects and advantages of the invention will become apparent hereinafter.

DETAILED DESCRIPTION

Even though the following description refers mainly to desks, the term "desk" as used herein can be applied equally well to other pieces of furniture to which a proprioceptive foot stimulator assembly as described herein could connect.

Figure 1:
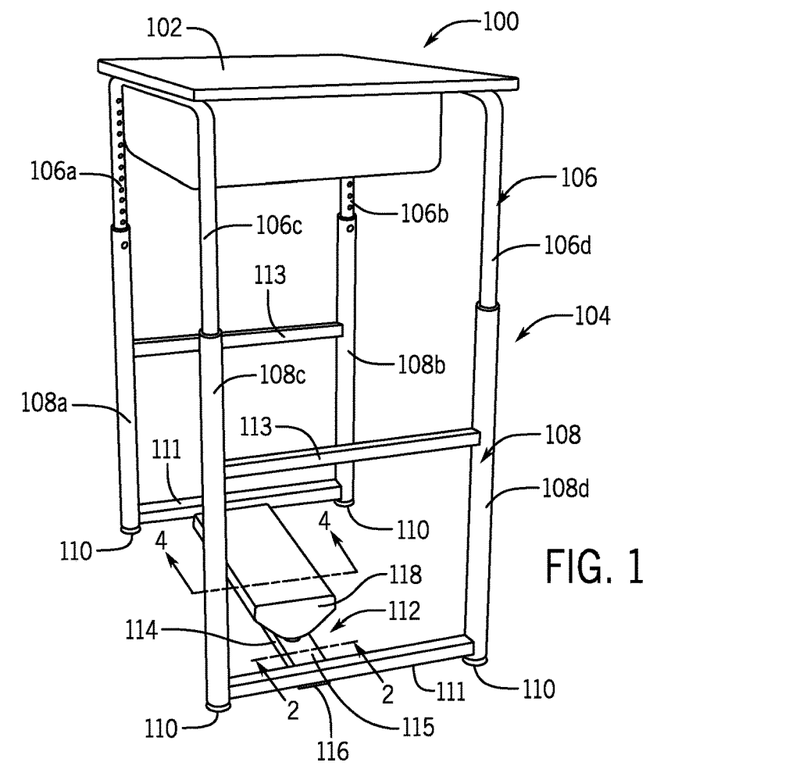
FIG. 1 is a perspective view of a desk with a proprioceptive foot stimulator assembly, according to one embodiment of the invention.

One aspect of the present invention provides a desk having a proprioceptive foot stimulator assembly connected to the desk. FIG. 1 shows a desk 100 having a work surface 102 supported by a leg structure 104. In this embodiment, the leg structure 104 has an upper frame 106 and a lower frame 108. The upper frame 106 includes at least one upper leg segment 106a-d, and the lower frame 108 includes at least one lower leg segment 108a-d. In certain embodiments, as shown in FIG. 1, the at least one lower leg segment 108a-d may rest on at least one attached adjustable glide 110 that increases the ease of moving the desk 100 across a floor surface.

In the embodiment shown, the leg structure 104 is a four-legged structure. In this embodiment, the upper frame 106 supports the work surface 102, and four upper leg segments 106a-d telescopically and slidably connect to four lower leg segments 108a-d, such that the upper frame 106 may be raised or lowered in relation to the lower frame 108. This allows the height of the work surface 102 to be adjusted to accommodate the height preferences of various sitting or standing individuals. In this embodiment, the upper leg segments 106a-d are of a smaller dimension than, and telescope into, the lower legs segments 108a-d. However, in other embodiments, the reverse arrangement may also be employed. Further, although the upper frame 106 and the lower frame 108 of this embodiment each include four leg segments, frames in other embodiments may include a different number of leg segments.

In the embodiment illustrated in FIG. 1, a set of lower support bars 111 and a set of upper support bars 113 are connected the lower leg segments 108a and 108b and to the lower leg segments 108c and 108d, respectively, to provide additional support to the leg structure. In this embodiment, the lower support bars 111 and the upper support bars 113 are connected to the lower leg segments 108a-d at ninety degree angles. However, in other embodiments, the lower support bars 111 and the upper support bars 113 may be connected to the lower leg segments 108a-d in different angular configurations. Further, some embodiments may include an increased or decreased number of support bars.

Although the desk 100 illustrated in FIG. 1 is height adjustable, desks in other embodiments may have a fixed-height construction. In such fixed-height embodiments, the leg structure 104 may have a single frame, with each leg being a unitary part, rather than having multiple connected frames. In a fixed-height embodiment, having only a single frame, the lower support bars 111 and upper supports bars 113 are connected to the single frame of the leg structure 104.

The embodiment illustrated in FIG. 1 further shows a proprioceptive foot stimulator assembly 112 connected to the desk 100. The proprioceptive foot stimulator assembly 112 has a foot stimulating member 118 pivotably connected to a cross bar 114. In this embodiment, the cross bar 114 has a pair of longitudinal ends 115 and is connected to the lower support bars 111 in a manner of fixed rotation at the longitudinal ends 115. In the embodiment shown, the cross bar 114 is comprised of a metal, such as steel, and is connected to the lower support bars 111 by a mounting flange 116 located at each longitudinal end 115. In the embodiment shown, the mounting flanges 116 are molded or otherwise integrally formed portions of the cross bar 114, while in other embodiments, the mounting flanges 116 may be affixed to the longitudinal ends 115 by means such as welding. Further, in certain embodiments, the mounting flanges 116 are bolted to the lower support bars 111. However, in other embodiments, a different means of connection besides bolting may be used to connect the mounting flanges 116 to the lower support bars 111. Additionally, in some embodiments, the longitudinal ends 115 may slidably connect to the support bars 111, in which case the longitudinal ends 115 can be placed at horizontally different portions along the lower support bars 111, for instance, by means of a roller track.

Figure 2:
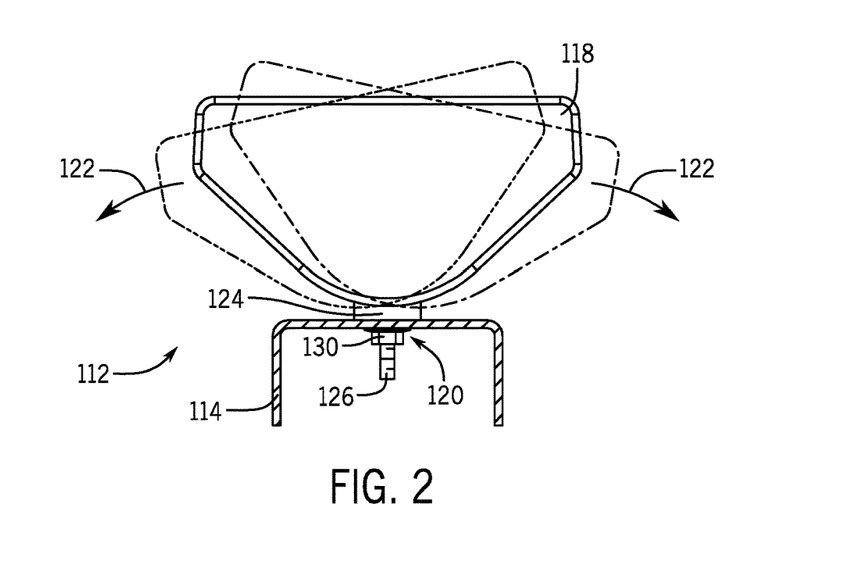
FIG. 2 is a sectional view of the foot stimulator assembly in FIG. 1, taken along line 2-2, showing a cross sectional view of a cross bar and a side view of a foot stimulating member and pivot assembly, showing in phantom certain different positions of the foot stimulating member.
Figure 3:
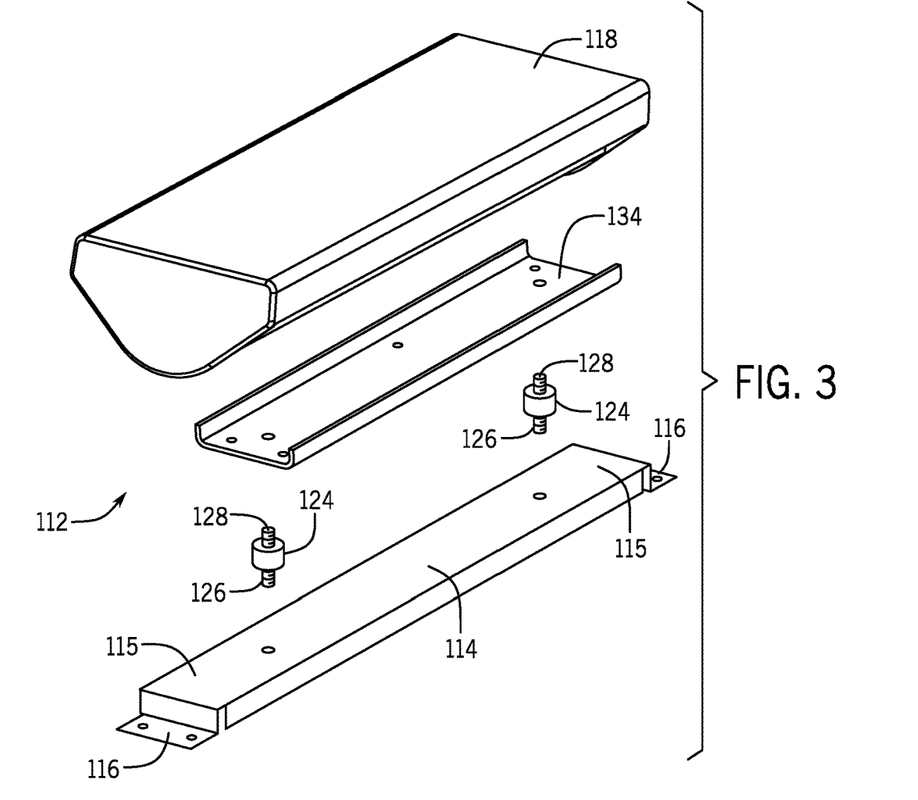
FIG. 3 is an exploded view of the proprioceptive foot stimulator assembly in FIG. 1.
Figure 4:
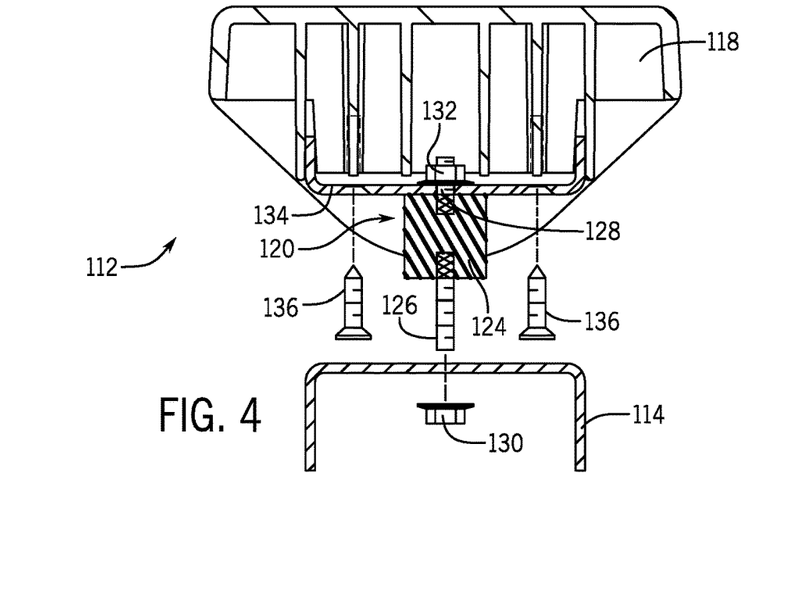
FIG. 4 is an exploded cross sectional view of the proprioceptive foot stimulator assembly in FIG. 1, taken along line 4-4.
Figure 5:
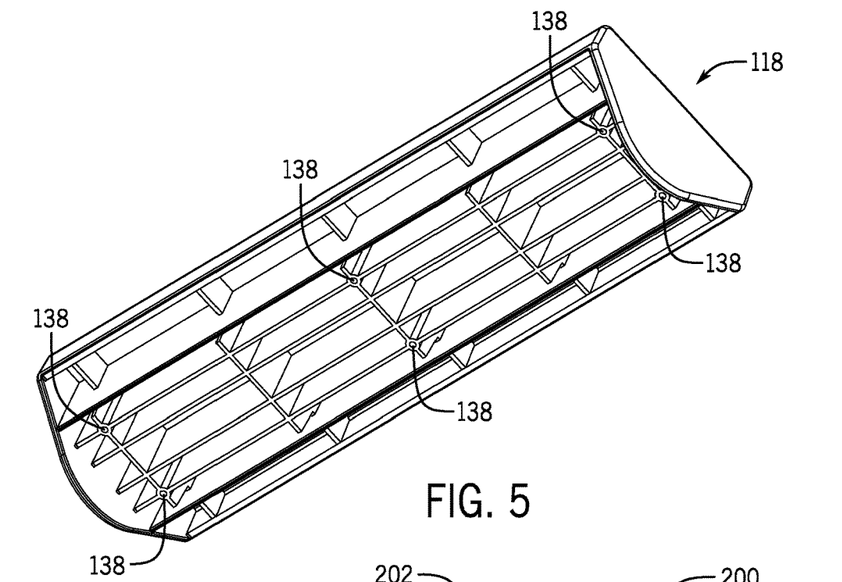
FIG. 5 is a bottom perspective view of the foot stimulating member that is part of the proprioceptive foot stimulating device in FIG. 1.

FIGS. 2-5 show the proprioceptive foot stimulator assembly 112 of FIG. 1 in greater detail. FIG. 2 shows a cross sectional view of the cross bar 114 and a side view of the foot stimulating member 118 pivoting in relation to the cross bar 114. A pair of arrows 122 and the phantom outlines of the foot stimulating member 118 represent the pivoting motion of the foot stimulating member 118. During standard use of the embodiment shown (the foot stimulating member 118 being pivoted by a user's foot), the foot stimulating member 118 can pivot up to forty-three degrees back and forth in either direction before contact with the cross bar 114 limits its angular motion. Other embodiments may allow a broader or narrower angular range of pivoting motion based on the size and shape of the foot stimulating member 118 and the proximity of the foot stimulating member 118 to the cross bar 114. FIG. 3 shows an exploded view of the proprioceptive foot stimulator assembly 112. FIG. 4 shows an exploded cross sectional view of the proprioceptive foot stimulator assembly 112. FIG. 5 shows a bottom perspective view of the foot stimulating member 118. In some embodiments, the proprioceptive foot stimulator assembly 112 may appear as an assembly alone, without being connected to a desk.

In the embodiment shown, as represented by the broken lines in FIG. 2, the foot stimulating member 118 pivots in relation to the cross bar 114 through use of a pivot assembly 120. In some embodiments, as shown in FIGS. 2-4, the pivot assembly 120 has a bushing 124 securing a first threaded fastener 126 and a second threaded fastener 128, along with a first lock nut 130 and a second lock nut 132. In certain embodiments, the bushing 124 is a rubber bushing, but other materials, besides rubber, that permit the pivot motion of the foot stimulating member 118, fall within the context of this invention. In this embodiment, as illustrated in FIG. 3, two bushings 124, relating to two pivot assemblies 120, are used. However, in other embodiments, a different number of bushings 124 or pivot assemblies 120 may be used.

When the proprioceptive foot stimulator assembly 112 is fully assembled, for each of the pivot assemblies 120, the first threaded fastener 126 is secured to the cross bar 114 by the first lock nut 130, the second threaded fastener 128 is secured to a bottom channel 134 by the second lock nut 132, and the bottom channel 134 is attached to the foot stimulating member 118. In some embodiments, as shown in FIG. 2, the cross bar 114 is formed as a channel, that is, open on a side opposite the location of the first threaded fastener 126, such that the first threaded fastener 126 may be freely accessed in order to add or remove the first lock nut 130.

Regarding the bottom channel 134, in certain embodiments, the bottom channel 134 is comprised of a metal, such as steel. In this embodiment, as shown in FIG. 4, the bottom channel 134 is attached to the foot stimulating member 118 by at least one screw 136. The screw 136 is secured in a hole 138 of the foot stimulating member, shown in FIG. 5. In the embodiment illustrated in FIG. 5, there are six holes 138 to receive six screws 136. However, in other embodiments, a different number of holes 138 or screws 136 may be used. Additionally, in other embodiments, other fastening elements may be used to connect the bottom channel 134 to the foot stimulating member 118.

Figure 6:
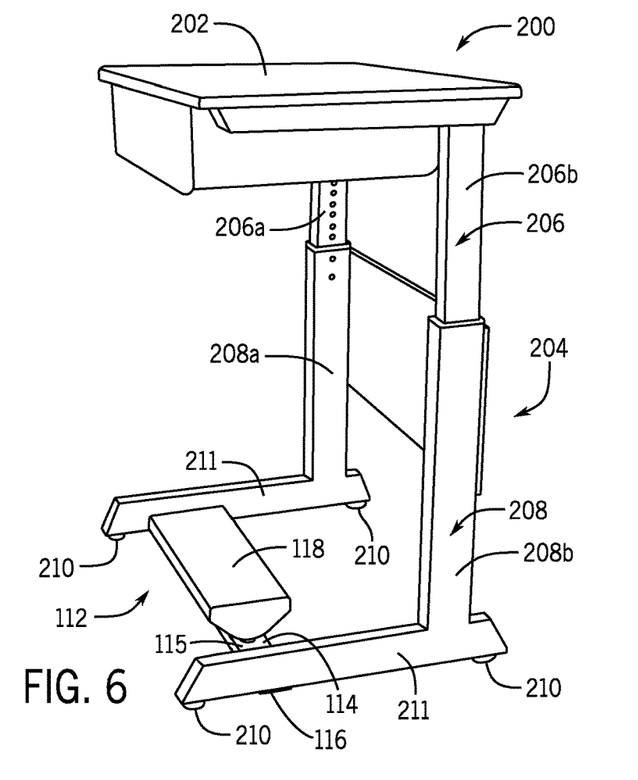
FIG. 6 is a perspective view of a desk with the proprioceptive foot stimulator assembly of FIG. 1, according to another embodiment of the invention.

FIG. 6 shows an alternative embodiment of the invention. In this embodiment, the proprioceptive foot stimulator assembly 112 of the previous embodiment is connected to a desk 200. In the embodiment shown, the leg structure 204 has an upper frame 206 and a lower frame 208. The upper frame 206 includes at least one upper leg segment 206*a-b*, and the lower frame 208 includes at least one lower leg segment 208*a-b*. In certain embodiments, as shown in FIG. 6, the at least one lower leg segment 208*a-b* may rest on an at least one attached adjustable glide 210 that increases the ease of moving the desk 200 across a floor surface.

In the embodiment shown, the leg structure 204 is a two-legged structure. In this embodiment, the upper frame 206 supports the work surface 202, and two upper leg segments 206*a-b* telescopically and slidably connect to two lower leg segments 108*a*-b, such that the upper frame 206 may be raised or lowered in relation to the lower frame 208. This allows the height of the work surface 202 to be adjusted to accommodate the height preferences of various sitting or standing individuals. In this embodiment, the upper leg segments 206*a-b* are of a smaller dimension than, and telescope into, the lower legs segments 208*a-b*. However, in other embodiments, the reverse arrangement may also be employed. Further, although the upper frame 206 and the lower frame 208 of this embodiment each include two leg segments, frames in other embodiments may include a different number of leg segments.

Additionally, in the embodiment shown, at least one foot 211 extends from lower leg segments 208*a-b* to provide additional support to the desk 200. Although in this embodiment the feet 211 are positioned generally parallel to a floor surface on which the desk rests and form perpendicular angles with lower leg segments 208*a-b*, in other embodiments, the feet 211 may have an incline or decline and may form non-perpendicular angles with the lower leg segments 208*a-b*.

In this embodiment, the cross bar 114 is comprised of a metal, such as steel, and is connected to the feet 211 by mounting flanges 116 located at each longitudinal end 115 of the cross bar 114. Although the mounting flange 116 is difficult to discern in FIG. 6, it is located in a similar position to that displayed in FIG. 1 in relation to the cross bar 114 and the member to which the cross bar 114 is connected. In this embodiment, the mounting flanges 116 are molded or otherwise integrally formed portions of the cross bar 114, while in other embodiments, the mounting flanges 116 may be affixed to the longitudinal ends 115 by means such as welding. Further, in certain embodiments, the mounting flanges 116 are bolted to the feet 211. However, in other embodiments, a different means of connection besides bolting may be used to connect the mounting flanges 116 to the feet 211. Additionally, in some embodiments, the longitudinal ends 115 may slidably connect to the feet 211, in which case the longitudinal ends 115 can be placed at horizontally different portions along the feet 211, for instance, by means of a roller track.

Although the desk 200 illustrated in FIG. 6 is height adjustable, desks in other embodiments may have a fixed-height construction. In such fixed-height embodiments, the leg structure 204 may have a single frame, rather than having multiple connected frames.

Figure 7:
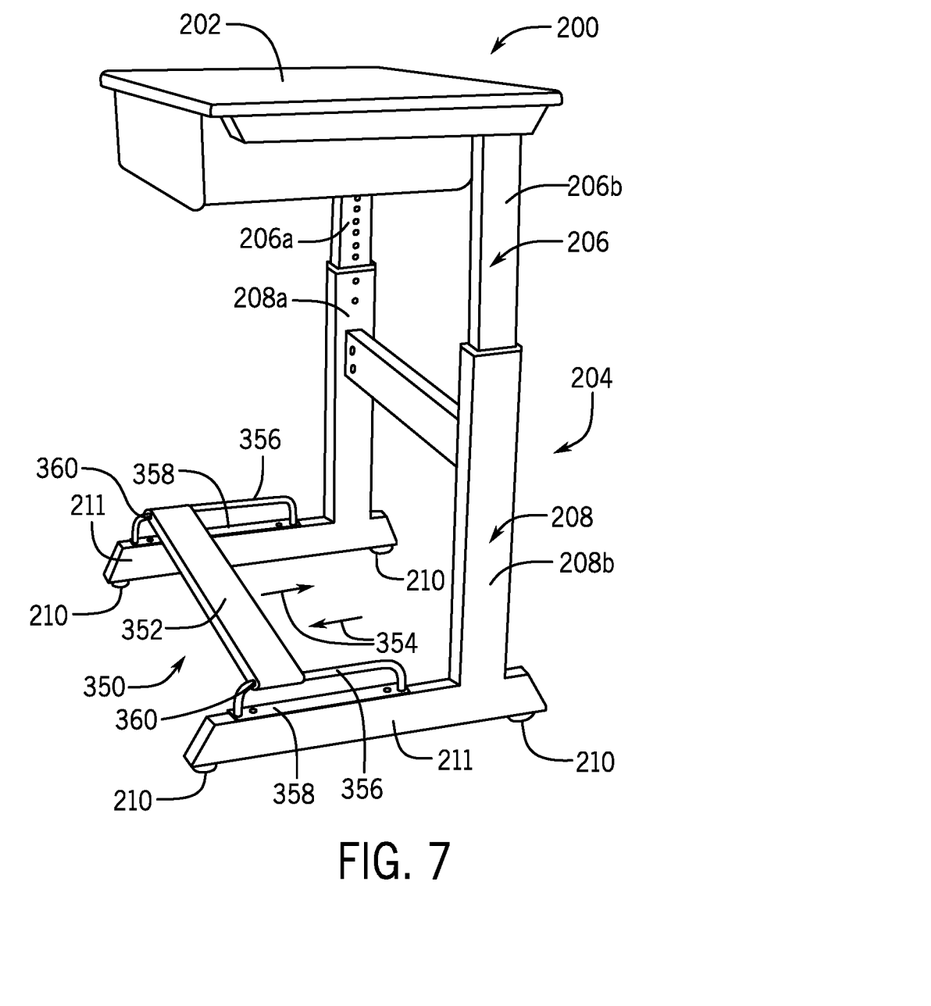
FIG. 7 is a perspective view of the desk of FIG. 6 with a proprioceptive foot stimulator assembly, according to another embodiment of the invention.

FIG. 7 shows another alternative embodiment of the invention. A proprioceptive foot stimulator assembly 350 is connected to the desk 200 of the previous embodiment. In this embodiment, a slider track 356 is connected to each of the feet 211. In certain embodiments, the slider track 356 is formed as a rod-like structure, which may be comprised of a metal, such as steel. In this embodiment, there are two slider tracks 356 that are placed parallel to one another, one on each of the two feet 211. However, in other embodiments, there may be a different number of slider tracks 356, and the slider tracks 356 may be skewed at different heights. In certain embodiments, as shown in FIG. 7, the slider track 356 is connected to the foot 211 by a plate 358. Also, in the embodiment shown, the slider track 356 has a center section that is relatively straight, with each end being curved so as to connect to plate 358. Other embodiments may also be used, such as wherein the plate 358 has upturned ends that reach upward to connect to the ends of the slider track 356.

Slidably connected to the slider track 356 is a foot stimulating member 352. In certain embodiments, the foot stimulating member 352 is made of a flexible plastic material. In this embodiment, at least one hole 360 is formed in the foot stimulating member 352. The hole is sized to permit the slider track 356 to pass through the hole 360, such that the foot stimulating member 352 may slide along the slider track 356. In the embodiment illustrated in FIG. 7, there are two holes 360, corresponding to the two slider tracks 356 of this embodiment, but other embodiments may have a different number of holes 360. Additionally, other embodiments may use other means of slidable connection. A pair of arrows 354 indicates the sliding movement of the foot stimulating member 352 when the foot stimulating member 352 is in use.

Although the invention has been herein described in what is perceived to be the most practical and preferred embodiments, it is to be understood that the invention is not intended to be limited to the specific embodiments set forth above. Rather, it is recognized that modifications may be made by one of skill in the art of the invention without departing from the spirit or intent of the invention and, therefore, the invention is to be taken as including all reasonable equivalents to the subject matter of the appended claims and the description of the invention herein.

What is claimed is:
1. A desk comprising:
   a work surface;
   a leg structure connected to and supporting the work surface; and
   a proprioceptive foot stimulator assembly connected to the leg structure and having:
      a cross bar having a first longitudinal end and a second longitudinal end, the first and second longitudinal ends being connected to the leg structure in positions of fixed rotation; and
      a foot stimulating member connected to the cross bar by a pivotable structure, such that the foot stimulating member is free to pivot in relation to the cross bar.

2. A desk as recited in claim 1 wherein the leg structure comprises an upper frame supporting the work surface and a lower frame, the upper frame and lower frame each having at least one leg segment, the at least one leg segment of the upper frame telescopically and slidably connecting to the at least one leg segment of the lower frame, such that the height of the work surface may be adjusted to accommodate the height preferences of various sitting or standing individuals.

3. A desk as recited in claim 2 wherein the lower frame comprises at least one support foot extending from the at least one leg segment of the lower frame.

4. A desk as recited in claim 1 wherein the foot stimulating member is limited from pivoting more than forty-three degrees back and forth in either direction.

5. A desk as recited in claim 1 wherein the first and second longitudinal ends of the cross bar are connected to the leg structure in a manner of fixed displacement.

6. A desk as recited in claim 1 wherein the first and second longitudinal ends of the cross bar are slidably connected to the leg structure.

7. A desk as recited in claim 1 further comprising a first mounting flange at the first longitudinal end of the cross bar and a second mounting flange at the second longitudinal end of the cross bar, the first and second mounting flanges attaching to the leg structure.

8. A desk comprising:
 a work surface;
 a leg structure connected to and supporting the work surface; and
 a proprioceptive foot stimulator assembly having:
  a first slider track member and a second slider track member connected to opposing sides of the leg structure; and
  a foot stimulating member, slidably connected to the first and second slider track members.

9. A desk as recited in claim 8 wherein the leg structure comprises an upper frame supporting the work surface and a lower frame, the upper frame and lower frame each having at least one leg segment, the at least one leg segment of the upper frame telescopically and slidably connecting to the at least one leg segment of the lower frame, such that the height of the work surface may be adjusted to accommodate the height preferences of various sitting or standing individuals.

10. A desk as recited in claim 9 wherein the lower frame comprises at least one support foot extending from the at least one leg segment of the lower frame.

11. A desk as recited in claim 8 wherein the foot stimulating member, having a first longitudinal end and a second longitudinal end, slidably connects to the first slider track member at the first longitudinal end and slidably connects to the second slider track member at the second longitudinal end.

12. A desk as recited in claim 8 wherein the first slider track member is positioned parallel to the second slider track member.

13. A desk as recited in claim 8 wherein the first slider track member is comprised of a first slider rod and the second slider track member is comprised of a second slider rod.

14. A desk as recited in claim 13 wherein the first slider rod and the second slider rod each have a first end portion and a second end portion parallel to the first end portion, the first and second end portions being connected to the leg structure, and the first end portion being connected to the second end portion by a middle portion perpendicular to the first and second end portions.

15. A desk as recited in claim 14 wherein the first slider rod is connected to the desk by a first plate and the second slider rod is connected to the desk by a second plate, the first and second end portions of the first slider rod being attached to the first plate and the first plate being attached to the leg structure, and the first and second end portions of the second slider rod being attached to the second plate and the second plate being attached to the leg structure.

16. A proprioceptive foot stimulator assembly adapted for use with a desk, the proprioceptive foot stimulator assembly comprising:
 a cross bar capable of being affixed to a desk, such that the cross bar is prevented from substantial movement with respect to the desk; and
 a foot stimulating member connected to the cross bar by a pivotable structure, such that the foot stimulating member is free to pivot in relation to the cross bar.

17. A proprioceptive foot stimulator assembly as recite in claim 16 wherein the foot stimulating member is limited from pivoting more than forty-three degrees back and forth in either direction.

18. A proprioceptive foot stimulator assembly as recited in claim 16, wherein the foot stimulating member includes a bottom channel, the bottom channel connected to the cross bar by the pivotable structure, such that the foot stimulating member is free to pivot in relation to the cross bar.

19. A proprioceptive foot stimulator assembly as recited in claim 18 wherein the pivotable structure comprises a pivot assembly having a first threaded fastener secured to the cross bar with a first lock nut, a second threaded fastener secured to the bottom channel with a second lock nut, and a flexible bushing, connecting the first threaded fastener to the second threaded fastener, such that the second threaded fastener is pivotable in relation to the first threaded fastener by means of flexure of the bushing.

20. A proprioceptive foot stimulator assembly as recited in claim 19 wherein the cross bar is open on a side opposite the first threaded fastener, such that the first threaded fastener may be freely accessed in order to add or remove the first lock nut.

21. A proprioceptive foot stimulator assembly adapted for use with a desk, the proprioceptive foot stimulator assembly comprising:
 a cross bar having a first longitudinal end and a second longitudinal end;
 a first mounting flange capable of being affixed to a desk located at the first longitudinal end of the cross bar;
 a second mounting flange capable of being affixed to a desk located at the second longitudinal end of the cross bar;
 a bottom channel pivotably attached to the cross bar by at least one pivot assembly, the at least one pivot assembly having:
  a first threaded fastener secured to the cross bar with a first lock nut;
  a second threaded fastener secured to the bottom channel with a second lock nut; and
  a flexible bushing, connecting the first threaded fastener to the second threaded fastener, such that the second threaded fastener is pivotable in relation to the first threaded fastener by means of flexure of the bushing; and
 a foot stimulating member attached to the bottom channel, the foot stimulating member being free to pivot in relation to the cross bar.

22. A proprioceptive foot stimulator assembly adapted for use with a desk, the proprioceptive foot stimulator assembly comprising:
 at least one slider rod having a first end portion capable of being affixed to the desk, a second end portion capable of being affixed to the desk, parallel to the first end portion, and a middle portion connecting the first end portion to the second end portion, the middle portion being perpendicular to the first and second end portions; and
 a foot stimulating member slidably connected to the at least one slider rod.

23. A desk as recited in claim 22 wherein the at least one slider rod is comprised of a first slider rod and a second slider rod, and the foot stimulating member, having a first longitudinal end and a second longitudinal end, is slidably connected to the first slider rod at the first longitudinal end and is slidably connected to the second slider rod at the second longitudinal end.

* * * * *